United States Patent [19]
Lieber

[11] Patent Number: 5,507,788
[45] Date of Patent: Apr. 16, 1996

[54] METHOD AND APPARATUS FOR CONTROLLING SKELETAL MUSCLE FATIGUE DURING ELECTRICAL STIMULATION

[75] Inventor: Richard L. Lieber, Carlsbad, Calif.

[73] Assignee: The Regents of the University of California, Oakland, Calif.

[21] Appl. No.: 289,011

[22] Filed: Aug. 11, 1994

[51] Int. Cl.⁶ ........................................ A61N 1/36
[52] U.S. Cl. ........................................ 607/48
[58] Field of Search ........................... 607/48, 49

[56] References Cited

U.S. PATENT DOCUMENTS

| | | | |
|---|---|---|---|
| 4,165,750 | 8/1979 | Aleev et al. | 128/422 |
| 4,177,819 | 12/1979 | Kofsky et al. | 128/422 |
| 4,236,528 | 12/1980 | Stanec et al. | 128/741 |
| 4,408,609 | 10/1983 | Axelgaard | 128/421 |
| 4,492,233 | 1/1985 | Petrofsky et al. | 128/421 |
| 4,499,900 | 2/1985 | Petrofsky et al. | 128/423 |
| 4,556,214 | 12/1985 | Petrofsky et al. | 272/117 |
| 4,569,352 | 2/1986 | Petrofsky et al. | 128/423 |
| 4,586,495 | 5/1986 | Petrofsky | 128/82.1 |
| 4,598,713 | 7/1986 | Hansjürgens et al. | 128/421 |
| 4,838,272 | 6/1989 | Lieber | 128/421 |

OTHER PUBLICATIONS

Petrofsky, Jerrold S. and Phillips, Chandler A., "Computer Controlled Walking in the Paralyzed Individual," *The Journal of Neurological and Orthopaedic Surgery*, 4:153–164, Jul. 1983.

Chang, Sheldon S. L., "Communication, Control, Devices, and Systems," *Fundamentals Handbook of Electrical and Computer Engineering*, II:90–91, 1983.

Lieber, Richard L. and Kelly, M. Jeanne, "Factors Influencing Quadriceps Femoris Muscle Torque Using Transcutaneous Neuromuscular Electrical Stimulation," *Physical Therapy*, 71:715–721, Oct. 1991.

Lieber, Richard L. and Kelly, M. Jeanne, "Torque History of Electrically Stimulated Human Quadriceps: Implication for Stimulation Therapy," *Journal of Orthopaedic Research*, 11:131–141, 1993.

*Primary Examiner*—William E. Kamm
*Attorney, Agent, or Firm*—Brown, Martin Haller & McClain

[57] ABSTRACT

A method and apparatus for applying electrical stimulation signals to muscles at a stimulation frequency which is varied in response to a detected ripple signal in an output tension or torque record which corresponds to the amount of fusion in the muscle contraction. An average torque amplitude is first determined as a stimulation signal is applied at an initial frequency, and the amplitude of the ripple on the torque output is determined and compared to the average torque amplitude to provide a ripple percentage. The measured ripple percentage is compared to a selected ripple percentage corresponding to the desired amount of fusion, and the stimulation frequency is adjusted by a feedback loop until the measured ripple percentage conforms to the selected value.

15 Claims, 6 Drawing Sheets

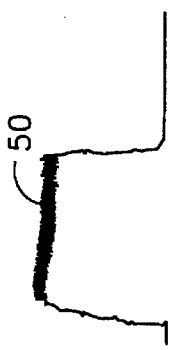
FIG. 2a 10 Hz
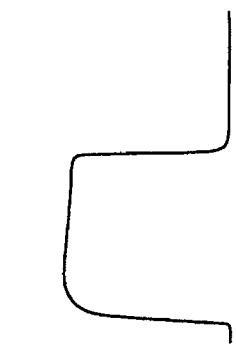
FIG. 2b 20 Hz
FIG. 2c 40 Hz
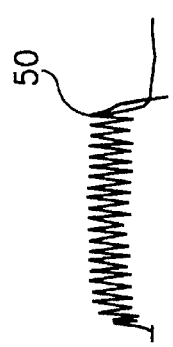
FIG. 2d 60 Hz
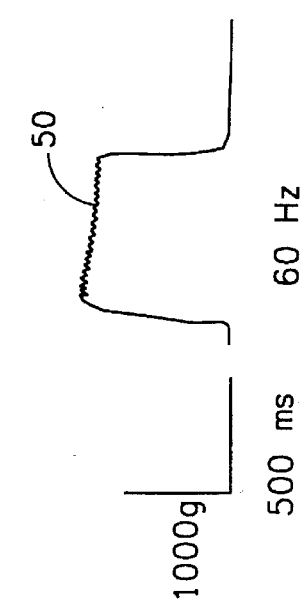
FIG. 2e 80 Hz
FIG. 2f 100 Hz
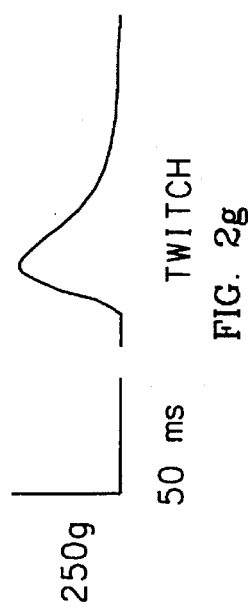
FIG. 2g TWITCH

METHOD AND APPARATUS FOR CONTROLLING SKELETAL MUSCLE FATIGUE DURING ELECTRICAL STIMULATION

BACKGROUND OF THE INVENTION

The present invention relates generally to a method and apparatus for electrically stimulating skeletal muscle, and is particularly concerned with a method and apparatus for controlling the amount of muscle fatigue resulting from such stimulation.

The use of electrical pulses or signals to induce muscle contractions and stimulate muscle movement or exercise is well known in the medical field. This technique is commonly known as neuromuscular electrical stimulation (NMES) and is often used in physical or occupational therapy, for example, to strengthen atrophied muscles or paralyzed limbs. NMES is widely used to exercise muscles that are immobilized for long periods of time as a result of paralysis, various muscular or neurological disorders, or extended periods of bed rest arising from injury, surgery, or illness. Such electrical stimulation is also useful for general exercise of otherwise functional muscles to improve muscle tone and strength.

Typically, in electrical stimulation therapy, an oscillating electrical signal is applied to the muscle at a frequency which stimulates muscular activity in the patient. One problem with such therapy is that it does not take into account individual variations between patients. Thus, the same signal may produce fatigue or overstimulation in one patient whereas the muscles of another patient are insufficiently exercised to produce a beneficial effect.

In my U.S. Pat. No. 4,838,272 a closed loop system is described in which electrical stimulation signals are applied to muscles and the work output by the muscles is determined and compared to a target value. The input stimulation signal is then varied according to the detected muscle work output in order to maximize the amount of work output by the muscles during a treatment period.

One problem with this feedback technique based on work output or muscle tension is that the nature of the tension change during electrical stimulation is not completely predictable and reproducible between individuals. Thus, at a given work output, the muscles of one individual may become over fatigued while another individual receives an optimum workout. Because of the variation in tension or work output between individuals, electrical stimulation systems using this factor as a feedback control must be customized for each individual to produce optimum results.

SUMMARY OF THE INVENTION

It is an object of the present invention to provide a new and improved method and apparatus for controlling muscle fatigue during electrical stimulation.

According to one aspect of the present invention, a method of exercising skeletal muscles is provided, which comprises the steps of applying to the muscles to be stimulated a series of stimulation signals having predetermined signal characteristics comprising signal frequency, amplitude and pulse width, so as to couple electrical energy into the muscles, detecting a torque output signal from the muscles as a result of the stimulation signals, measuring the average peak amplitude of the output signal, measuring the amplitude of a ripple on the output signal, comparing the measured ripple amplitude to the average peak torque amplitude to obtain a ripple percentage, comparing the ripple percentage to a selected value, and adjusting the stimulation frequency of subsequently applied stimulation signals in response to the detected ripple percentage being different from said selected value.

This method makes use of detected individual muscle contractions or ripples on the output torque signal in order to provide a feedback signal for controlling the input stimulation signal. When a series of electrical pulses is applied to a muscle, the resultant force generated by the muscle is dependent on the amplitude of the applied signal and the frequency of that signal. The first input pulse or stimulus will cause contraction and subsequent relaxation of the muscle. If the next pulse arrives before the muscles can completely relax, a greater force will be generated at the ends of the muscle fiber. This is because the first stimulus will cause the contracting sarcomeres to "stretch out" the passive structures that lie in series with them, e.g. the tendons or passive sarcomeres. When the second impulse or stimulus arrives at the scene, it is not required to stretch out any of these structures and causes a greater force to be generated. Thus, two impulses of the same magnitude delivered to a muscle and separated by, say, 50 msec will result in more force than the same two impulses separated by a greater time interval. When a train of pulses is delivered, a tetanic contraction is produced.

At relatively low stimulation frequencies, the contractile record almost completely relaxes between pulses, with the result that the ripple amplitude will be substantially equal to the force amplitude. As frequency increases, the ripple signal will become smaller and smaller, until eventually a fused tetanic contraction is produced in which individual contractile events cannot be distinguished and no ripple is seen on the output signal. This is known as a fused tetanic contraction, and this occurs because the repeated calcium release events onto the myofilaments are much faster than the rate at which the myofilaments can contract and then relax.

The ideal stimulating frequency will be somewhere between these two extremes. At low frequency, insufficient force will be generated by the muscle to have any beneficial effect. At very high frequency, fatigue will occur. The frequency at which the tension record fuses will vary between individuals, and will even vary in the same individual as the muscle fatigues. By basing the feedback on the ratio between the ripple amplitude and the force amplitude, or the percentage of ripple, the same basic system can be used to control stimulation parameters in a reproducible manner between individuals. The amplitude of the ripple signal as a percentage of the total signal or force amplitude provides an absolute measure of the fatigue. Preferably, the selected percentage is in the range from 10% to 20%, and the frequency of the stimulation signal is varied so as to maintain the ripple amplitude in this range.

By using the ripple signal as an index of the relative tension level, instead of the absolute tension magnitude, and providing feedback based on the relative magnitude of the ripple signal, a number of advantages are obtained. First, the ripple signal is extremely clean and easy to analyze by high-pass filtering of the muscle output tension record. Even if the subject moves, the ripple trace remains the same, simply shifting up or down, and this DC shift is invisible after filtering. Secondly, this technique automatically accounts for fiber type variation between individuals, and inherently determines the most appropriate stimulation frequency signal for each individual. This ensures that substantially the optimal amount of muscle work is performed by all individuals treated. Also, as the individual being treated becomes fatigued, resulting in more fusion for the same input frequency, the frequency will be automatically reduced to control muscle fatigue.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which:

FIGS. 2(a)–2(f) are graphic representations of contractile muscle output records as a result of stimulation pulses of gradually increasing frequency, from completely unfused to completely fused;

FIG. 2(g) is a graphic representation of a single muscle twitch output;

DESCRIPTION OF THE PREFERRED EMBODIMENT

Figure 1:
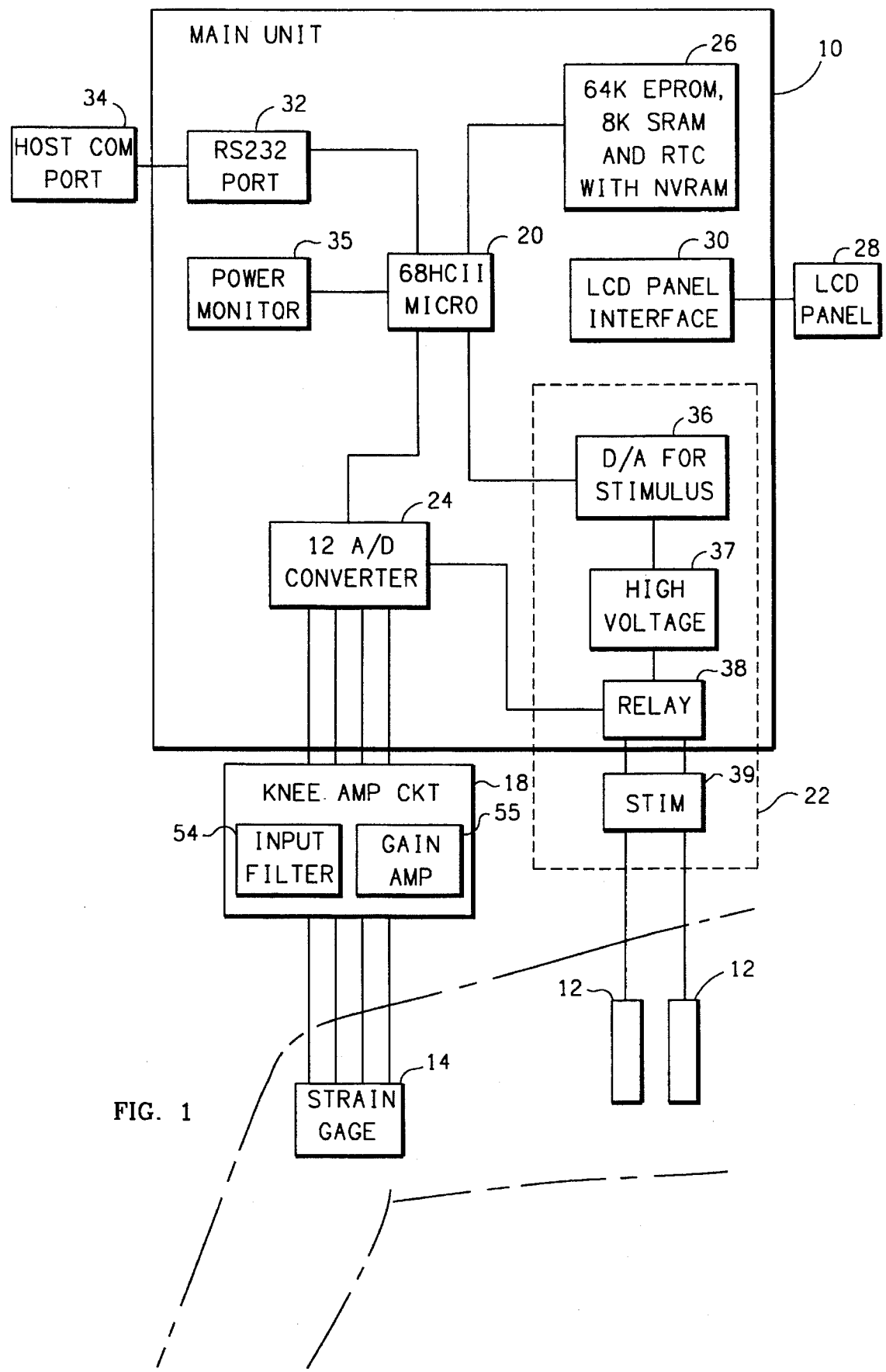
FIG. 1 is a schematic block diagram illustrating a muscle stimulating apparatus according to a preferred embodiment of the invention.
Figure 3:
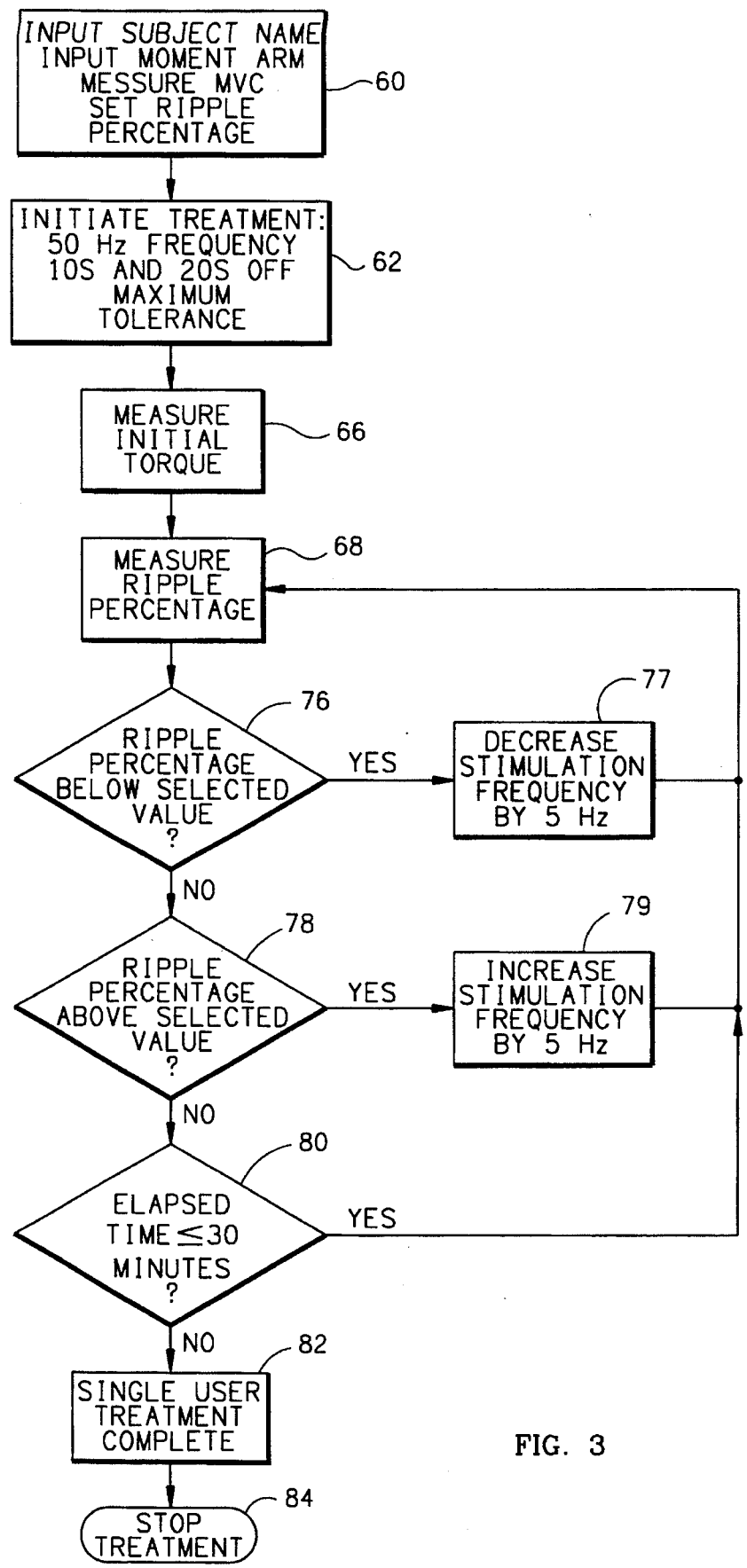
FIG. 3 is a flow chart illustrating the steps in a method of muscle stimulation according to the preferred embodiment of the invention using the apparatus of FIG. 1.

FIG. 1 illustrates a muscle stimulation apparatus according to a preferred embodiment of the present invention for applying a series of electrical pulses to selected muscle areas and at a frequency controlled according to the method as illustrated in FIG. 3.

The apparatus basically comprises a control unit 10 which controls a stimulation signal applied to stimulation pads 12. The pads 12 may be secured at an appropriate position on a patient's limb by straps, adhesive tape, conductive suction cups or the like as is conventional in the field. The pads 12 are preferably reusable, self adhering electrodes, but may alternatively be transcutaneous electrodes, carbonized rubber electrodes or sponge electrodes as are known in the art. Pads 12 are secured at the appropriate position on a patient's or subject's body in order to stimulate the desired muscle or muscle group. For example, in the illustrated embodiment the pads 12 are secured over the subject's quadriceps femoris musculature.

A torque measuring device or transducer 14 is applied to the joint on which the treated muscles insert to produce an output torque signal. Device 14 may be applied via a strap or brace arrangement, as is conventional in the field, to any joint such as the knee joint 16 as illustrated, or an ankle joint. Device 14 is coupled to the joint on which the muscles insert in order to determine the amount of torque exerted by the muscles during stimulation and put out an output signal representing the variation of torque with time. The transducer device 14 is connected to the skin surface adjacent the muscles and may be extended lengthwise between opposite sides of the muscle group, or across the related joint structures, for example across the knee joint as illustrated in FIG. 1.

Figure 6:
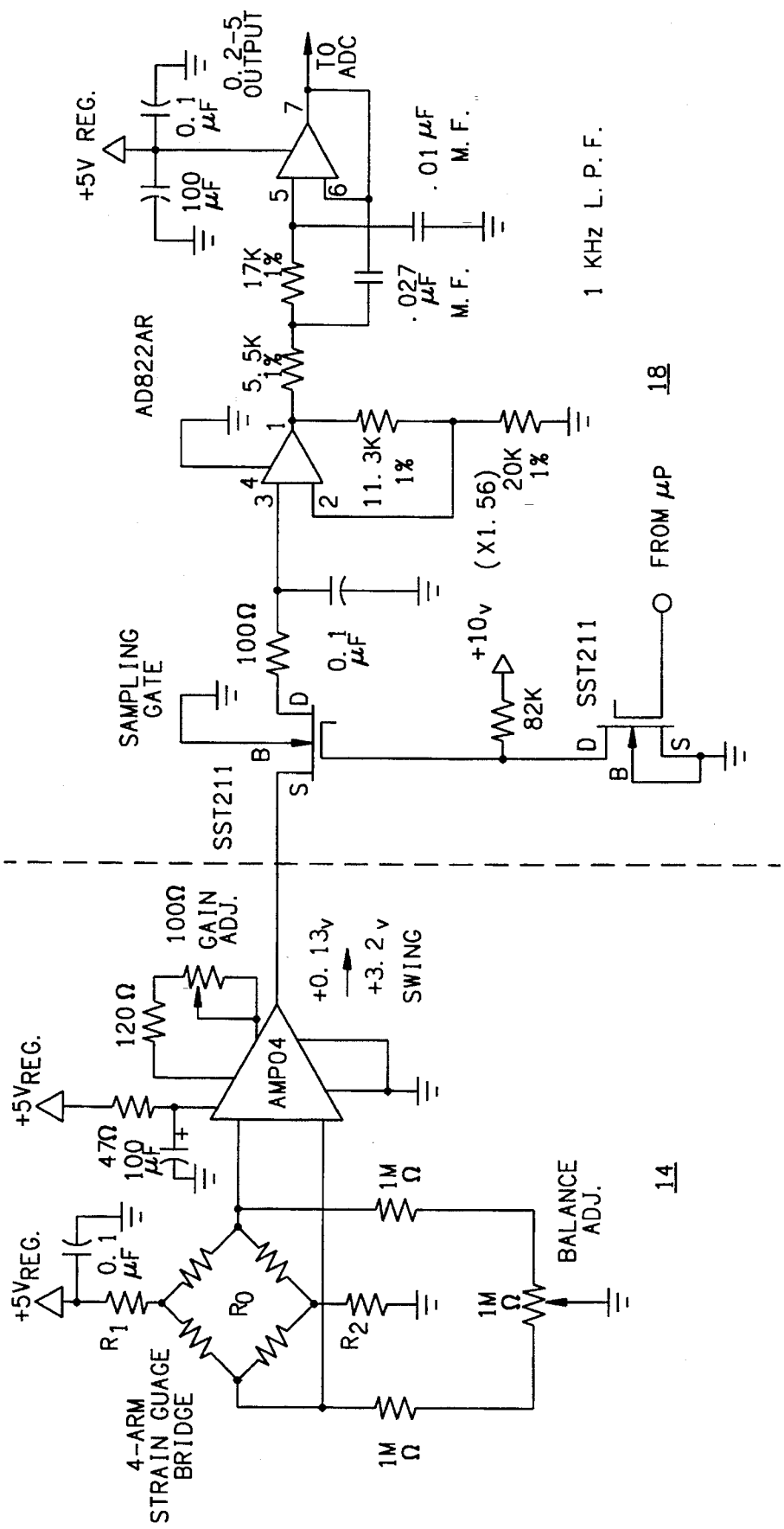
FIG. 6 is a schematic block diagram illustrating the strain gage and strain gage signal conditioning circuitry in more detail.

A variety of torque measuring devices for use in stimulation therapy are known to those skilled in the art and may be used in the apparatus. However, in a preferred embodiment of the invention a custom-made torque measuring device as illustrated in more detail in FIG. 6 is used in this apparatus. This device is a strain gauge wheatstone bridge of sufficient sensitivity to detect a ripple signal at frequencies up to 100 Hz. The torque measuring device 14 is connected to a knee amplifier circuit 18, and the output of amplifier circuit 18 is connected to unit 10. The torque measuring device may alternatively be attached to the subject's ankle, with the distance between the attachment strap and the knee joint being measured and used as a moment arm.

Control unit 10 includes microprocessor 20 for controlling the stimulation signal based on feedback from the torque measuring device, as described in more detail below in connection with FIG. 3, as well as the stimulator 22 for producing the stimulation signal to be applied to pads 12, and an analog to digital converter 24 for the knee amplifier output. Microprocessor 20 is connected to memory 26 containing program instructions for performing the method steps of FIG. 3 as well as other stored data. A suitable output display device 28 is also connected to the microprocessor 20 in a conventional manner via interface 30. An RS-232 serial port 32 is provided for selective connection to a host computer via port 34 for host computer communications. A power monitor 35 is provided for low voltage detection.

The stimulator 22 is arranged to produce an output stimulation signal at a selected amplitude, pulse frequency, pulse width and duration. The stimulator 22 is connected to the output of microprocessor 20 in a conventional manner via digital to analog converter 36 to convert the digital output of controller or processor 20 to an analog signal, high voltage stimulus output circuitry or power supply 37 for producing the stimulation signal, a multi-plexing relay 38 for signal routing, and stimulation amplifier 39. Stimulator 22 produces an analog stimulation signal at the pads 12 at an amplitude of the order of 10 to 50 volts and at a selected frequency in the range of 10 to 100 Hertz. Some examples of suitable circuitry for implementing the stimulator are shown in U.S. Pat. Nos. 4,499,900, 4,556,214 and 4,569, 352, for example. In a preferred embodiment of the invention, the stimulator 22 comprises circuitry as illustrated schematically in FIG. 5 which will produce the desired output stimulation signal.

Figure 5:
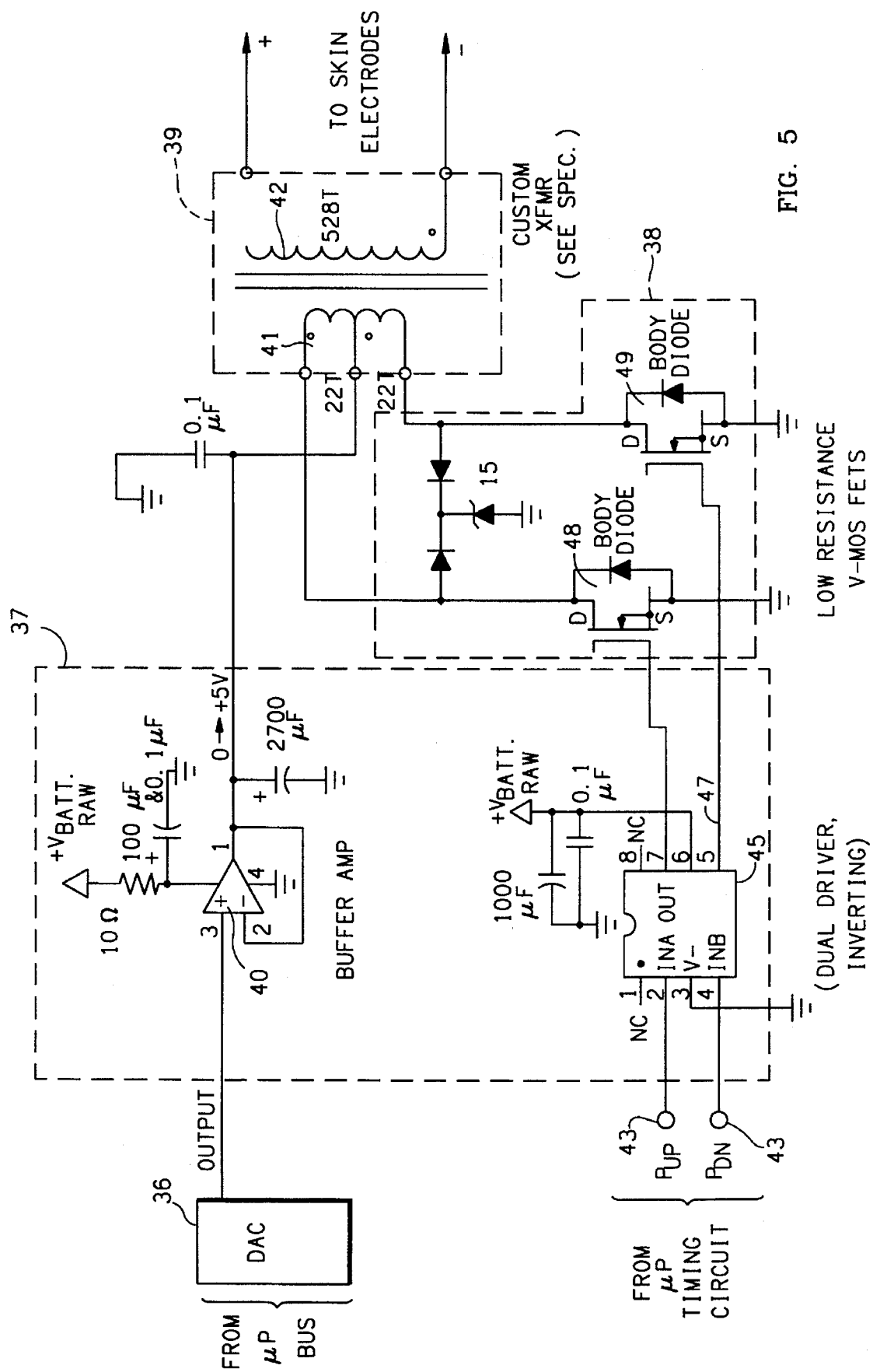
FIG. 5 is a schematic block diagram illustrating the electrode pulse generator of FIG. 1 in more detail.

As illustrated in FIG. 5, the output of digital to analog converter 36 is connected via buffer amplifier 40 to the center tap of input winding or coil 41 of a custom transformer or stimulation signal amplifier 39. Input winding is of 44 Tesla, while output winding 42 is of 528 Tesla and is connected to the skin electrodes 12. Microprocessor timing circuits have outputs 43 connected to input pins of an integrated circuit 45, preferably an ICL 7667, comprising an inverting dual driver. Outputs 46, 47 of the integrated circuit 45 are connected to low resistance V-Mos FETs or field effect transistors 48,49 forming a multi-plexing relay 38, the outputs of which are connected across the winding 41 of the transformer 39. This produces the desired output stimulation signal of selected amplitude, pulse frequency, pulse width and duration at the electrodes 12, as will be understood by those skilled in the field.

The torque transducer 14 detects the force exerted by the muscles during stimulation and provides an output signal proportional to the torque generated. The knee amplifier circuit 18 provides interface and amplification between the strain gauge or transducer 14 and the central processing unit.

FIGS. 2(a)–(f) illustrate typical force outputs with time, or muscle contractile records, over a range of different input signal frequencies. FIG. 2(a) illustrates the variation of muscle force with time for and input signal of 10 Hz, while FIG. 2(b) illustrates the torque record for a 20 Hz input, FIG. 2(c) illustrates the record for a 40 Hz input, FIG. 2(d) illustrates the record for a 60 Hz input, FIG. 2(e) illustrates the record for a 80 Hz input, and FIG. 2(f) illustrates the record for a 100 Hz input stimulation signal.

When an input signal is applied at a relatively low frequency to a muscle, the muscle will have time to relax completely between stimulating pulses. In this case, the force signal will have ripples or pulses 50 as illustrated in FIG. 2(a) corresponding to the stimulating pulses and having an amplitude (A) which is more or less equal to the peak muscle force amplitude. When the peak to peak amplitude of the ripple signal 50 is equal to the peak output torque, the ripple percentage is said to be 100%, and the muscle will twitch as illustrated in FIG. 2(g).

If the input signal frequency is now increased to 20 Hz, the muscle will not have time to relax completely between stimulating pulses and the mechanical twitches will start to fuse. The first stimulating pulse will cause the contracting sarcomeres to stretch out the passive structures that lie in series with them, and if the second stimulating pulse arrives before the contracting sarcomeres have relaxed, it will not be required to stretch out these structures. Thus, a greater force will be generated at the ends of the muscle fiber. Thus, as illustrated in FIG. 2(b), the ripple amplitude will be reduced while the peak muscle force increases. At this frequency, the ripple percentage is around 80% or 90%. As the frequency is increased further, to 40 Hz, the output signal of FIG. 2(c) is produced in which the peak force amplitude is increased while the ripple amplitude is decreased. The ripple amplitude continues to decrease as the stimulation frequency is increased, until at very high frequency the record becomes completely fused, or a fused contraction, in which it is impossible to detect any individual pulses in the output signal. A fused contraction is illustrated in FIG. 2(f), and in the illustrated example fusion has occurred at an input stimulation frequency of 100 Hz. This corresponds to a ripple percentage of 0%. The frequency at which fusion occurs will vary between individuals, and will also decrease in the same individual as the muscle becomes increasingly fatigued.

In order to ensure that a selected muscle area is worked hard enough to produce a beneficial effect, but at the same time not so hard that the muscle becomes excessively fatigued, in this invention the ripple percentage of the muscle output signal is monitored and used to control the input stimulation frequency in order to maintain the ripple percentage in a selected range. Preferably, the ripple percentage is maintained in the range from around 10% to 20% in order to produce an optimum muscle workout.

The torque transducer 14 must be sensitive enough to detect a high frequency ripple 50 on the muscle output, and is made stiff enough to respond to high frequencies of the level encountered in electrical stimulation therapy. Preferably, as mentioned above, the transducer 14 is a strain gauge wheatstone bridge 52 and is connected to circuitry 18 for conditioning and amplifying the signal, as illustrated in more detail in FIG. 6. The output of circuit 18 is connected to the analog to digital converter 24, as illustrated in FIG. 1.

The output of wheatstone bridge 52 is connected via adjustable gain amplifier 53 to the signal conditioning and amplifier circuit 18, which basically comprises a 1 KHz low pass filter 54 and gain amplifier 55.

Figure 4:
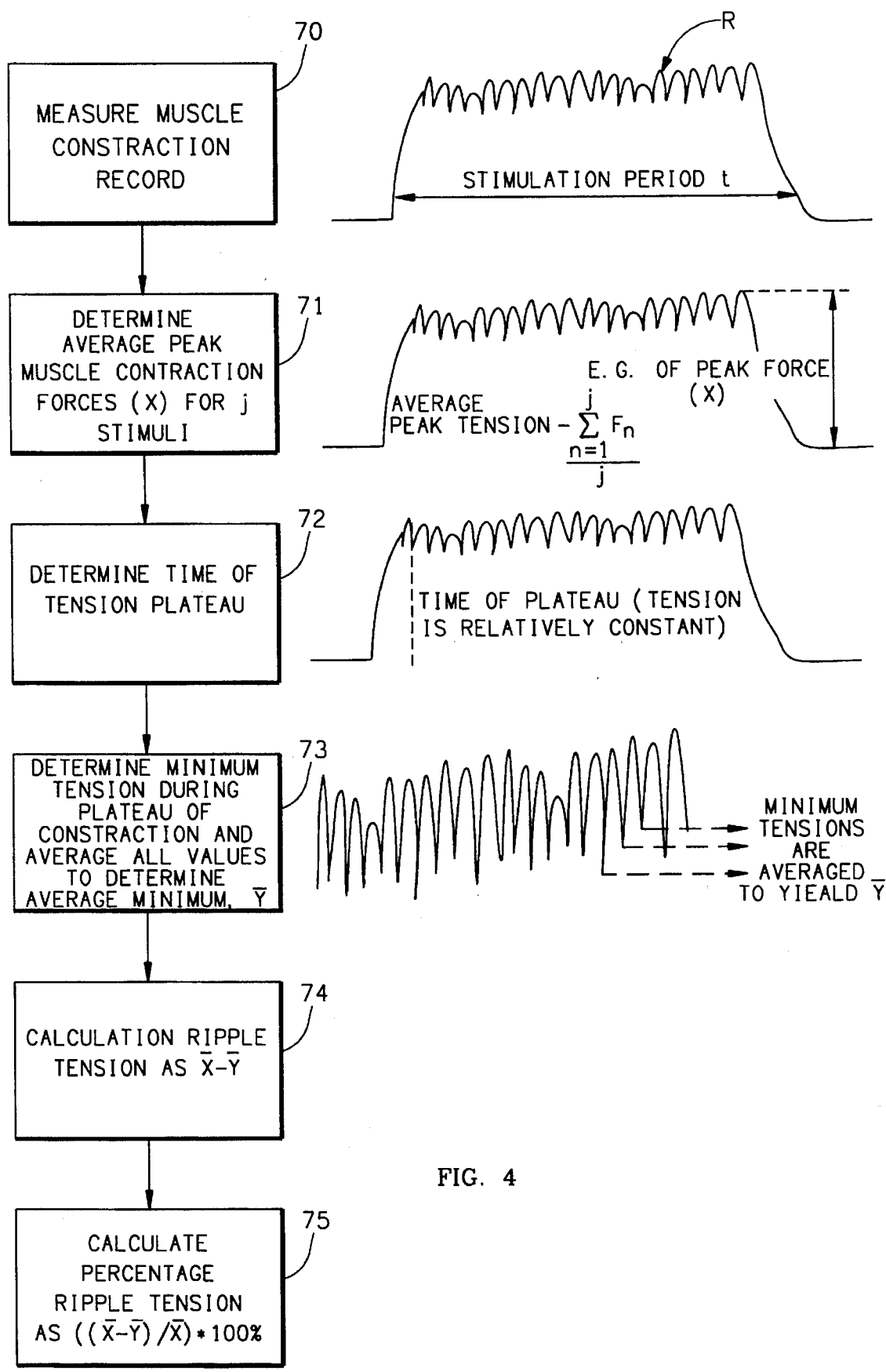
FIG. 4 is a flow chart illustrating the steps in measuring the ripple percentage in more detail.

The method of controlling the stimulation signal based on the detected ripple percentage is illustrated schematically in flow chart form in FIGS. 3 and 4. The controller or microprocessor is suitably programmed by program instructions stored in memory 26 to control the system to perform the listed steps, as will be understood by those skilled in the field. The method is a closed loop feedback process based on measured ripple percentage in the output signal.

In the first stage or step 60, a number of individual measurements are taken and input for data storage. The knee extension moment arm, or distance from the lateral femoral condyle to the middle of the transducer strap, is measured and entered in step 60, along with the name of the subject and any other desired measurements. The maximum voluntary contraction, or MVC, for the subject is then measured, if appropriate, by asking the subject to extend the knee joint and measuring the resultant output torque. This value provides information to the physician as to progress made during treatment. The desired ripple percentage is also selected and entered at this stage, which may be in the range of 10% to 20%, for example.

At step 62 a number of other stimulation pulse parameters are selected and entered, as in any stimulation protocol. These parameters include the frequency of the stimulation signal, the on period of the stimulation signal, the off period of the stimulation signal, the maximum tolerance, amplitude, and so on. The stimulation frequency chosen initially is from the range known to induce muscle contraction in human patients. A typical frequency range for physiologically induced muscle contractions is in the range of 10 to 100 Hz. In the illustrated example, an initial frequency of 50 Hz is selected, although it will be understood that other frequencies within the desired range may be chosen as the initial stimulation signal frequency. In previous muscle stimulating devices, for example as described in my U.S. Pat. No. 4,838,272, it was necessary to test each patient before starting treatment to determine a fusion frequency for that individual. With the feedback process of this invention, the frequency is automatically adjusted to the ideal response range for each individual, avoiding the need for prior testing of the frequency response.

In a typical muscle stimulation protocol, the stimulation signal is applied for a selected time period, then turned off for a selected rest or off period, then applied for the selected on period, and so on. In the illustrated example, the selected on period is 10 seconds and the off or rest period between stimulation periods is 20 seconds, although it will be understood that other time periods may be selected in alternative embodiments.

The output torque signal received from the torque transducer will be a waveform of the type illustrated in FIGS. 2(a)–2(f), and the initial torque or peak torque amplitude can be calculated from the output signal. This calculation is performed at step 66. The ripple percentage is then calculated in step 68, as illustrated in more detail in FIG. 4, which illustrates the steps in calculating a ripple percentage from an output torque signal. As illustrated in FIG. 4, the muscle contraction record R over a stimulation period t is first produced in step 70. In step 71, the record R is used to determine the average peak tension $\overline{X}$ over a series of j stimulation pulses, according to the algorithm:

$$\text{Average Peak Tension } (\overline{X}) = \frac{\sum_{n=1}^{j} Fn}{j}$$

where Fn is the peak tension produced by the nth pulse.

In step 72, the time of the tension plateau is determined, in other words the time for which the tension remains relatively constant. In step 73, the average minimum tension $\overline{Y}$ is determined by determining each minimum tension during the record or plateau of the contraction, and determining the average of all minimums.

The average ripple tension is then determined in step 74 by subtracting Y from X, in other words: Average ripple tension =Average Peak tension ($\overline{X}$)— Average minimum tension ($\overline{Y}$).

Finally, in step 75, the ripple percentage is determined according to the following relationship:

$$\text{Ripple Percentage} = ((\overline{X} - \overline{Y})/\overline{X}) * 100\%$$

Preferably, the peak torque amplitude, the ripple amplitude and the ripple percentage are calculated digitally by stored program instructions, as illustrated in FIG. 4, although it will be understood that analog means may be used to generate the same outputs. Peak torque is calculated in a conventional manner as is known in the stimulation field. The ripple amplitude may be generated by analog or digital high pass filtering of the tension record.

After the ripple percentage has been determined in step 68 according to the steps illustrated in FIG. 4, the measured ripple percentage is compared to the selected ripple percentage. First, the program determines if the ripple percentage is below the selected value (step 76). If it is below the selected value, the program proceeds to step 77, which causes the stimulation frequency to be reduced by 5 Hz. The new, lower stimulation frequency is now caused to stimulate the muscles, which should increase the ripple amplitude as discussed above, and the program returns to step 68 to perform the procedure for measuring the ripple percentage again. If the measured ripple percentage at step 76 is determined not to be below the predetermined value, the program proceeds to step 78. At step 78, a determination is made as to whether the measured ripple percentage is above the selected ripple percentage. If the answer to this is YES, the stimulation frequency is increased by 5 Hz at step 79, and the new, higher stimulation frequency is used to stimulate the muscles, resulting in reduced ripple amplitude as discussed above. After a change in the stimulation frequency at either step 76 or step 78, the program returns to step 68 to determine the new ripple percentage as a result of the modified stimulation frequency. This forms a closed feedback loop for controlling the ripple amplitude by adjusting stimulation frequency.

If the answer at both step 76 and 78 is NO, this means that the measured ripple percentage is equal to the selected ripple percentage, and the elapsed time is then checked at step 80. If the elapsed time is less than or equal to a selected treatment period (typically 30 minutes to avoid undue fatigue in the subject), the stimulation is continued and the ripple percentage is again measured at step 68, and the feedback loop continues.

It can be seen that with this feedback technique, the ripple percentage is constantly monitored and compared to a selected value, and if the ripple percentage is above or below the desired value the input frequency is varied up or down until the measured ripple percentage is at the desired level. The ripple percentage will vary even when the input frequency remains constant for a time, as a result of muscle fatigue, and this feedback technique ensures that the stimulation frequency is progressively reduced as the muscle becomes fatigued, reducing muscle fatigue so that a treatment period can be completed before muscle fatigue becomes excessive.

The feedback loop continues until the selected treatment period is completed (82), as determined by checking the elapsed time at preceding step 80. Once the elapsed time period is determined to be greater than 30 minutes, an output signal is produced indicating treatment is complete (step 82) and the treatment is stopped, turning off the stimulator (step 84).

Although the above method controls the stimulation frequency to adjust the ripple percentage to a selected single value, the method may instead adjust the ripple percentage to lie in a selected ripple percentage range, for example 10% to 20%. In this case, step 76 will determine whether the measured percentage is below the minimum value in the range and step 78 will determine whether the measured percentage is above the maximum value in the range. Also, it will be understood that the ratio between peak torque amplitude and ripple amplitude may be used for feedback control instead of the percentage.

This provides a new method for controlling the work performed by muscles during stimulation therapy based on the amplitude of the ripple signal produced during stimulation, rather than the absolute tension magnitude as was done in the past. The ripple signal provides a better indication of muscle fatigue than the absolute tension magnitude, since the nature of the tension change during electrical stimulation is not completely predictable between individuals. This new method, which is based on the relative fusion of the tension record, rather than absolute tension, is much more stable and reproducible between individuals, and permits a more powerful feedback to control stimulation parameters. The ripple signal is extremely clean and easy to analyze by high-pass filtering the tension record, using digital or analog techniques. Even if the subject moves, causing DC shift of the signal, the ripple trace will remain the same, simply shifting up or down. The shift will be invisible after high pass filtering.

As has been noted above, the frequency at which the tension record fuses varies between individuals, so whereas one individual will become overly fatigued at a certain stimulation frequency, others may be under-exerted. Thus, up to now, it has been necessary to generate a fusion frequency curve for each treated individual to determine which stimulation frequency is most appropriate for each individual. With this technique, the most appropriate stimulation frequency is generated automatically for each individual, much faster than was previously possible. Additionally, this technique allows for progressive fatigue of the muscle as treatment proceeds, adjusting the stimulation frequency as appropriate to control fatigue. This permits much better control of muscle fatigue during stimulation therapy.

The method described above involves stimulation of a single muscle group and stimulation signal output. It will be understood that the same method may be used for stimulating any desired muscle group or multiple muscles or muscle groups simultaneously. The use of data storage circuitry or memory circuits allows the torque and ripple percentage measurements for each patient to be stored along with the varying stimulation frequency and other stimulation parameters for future display, storage or conversion to a printed output as desired. This allows efficient monitoring of system operation, patient progress, patient compliance and the like.

Although a preferred embodiment of the invention has been described above by way of example only, it will be understood by those skilled in the field that modifications may be made to the disclosed embodiment without departing from the scope of the invention, which is defined by the appended claims.

I claim:

1. A method of exercising skeletal muscles, comprising the steps of:

applying to a muscle or muscles to be stimulated a series of stimulation signals having selected signal characteristics including stimulation frequency and amplitude so as to couple electrical energy into the muscles;

detecting a torque output signal from the muscles as a result of the input stimulation signals;

measuring the average peak torque amplitude of the output signal;

detecting a ripple signal on the torque output signal;

measuring the amplitude of the ripple signal;

determining a ripple percentage from the measured ripple and average peak torque amplitudes;

comparing the determined ripple percentage to a selected ripple percentage; and adjusting the input stimulation frequency if the ripple percentage is different from the selected ripple percentage.

2. The method as claimed in claim 1, wherein the step of comparing the determined ripple percentage to a selected ripple percentage comprises determining whether the determined ripple percentage is greater than or less than the selected ripple percentage, and the step of adjusting the input stimulation frequency comprises incrementing the frequency up or down by a selected increment if the determined ripple percentage is greater than or less than the selected ripple percentage, respectively.

3. The method as claimed in claim 2, wherein the increment is 5 Hertz.

4. The method as claimed in claim 1, wherein the initial frequency is 50 Hertz.

5. The method as claimed in claim 1, including the step of returning to the ripple percentage determining step after each input stimulation frequency adjustment.

6. The method as claimed in claim 1, wherein the selected ripple percentage is in the range from 10% to 20%.

7. A method of exercising skeletal muscles, comprising the steps of:

applying a series of stimulation signals to selected muscles, the signals having a selected initial stimulation frequency and amplitude;

detecting the torque output by the muscles in response to the stimulation signals;

measuring the average peak torque amplitude;

detecting a ripple signal on the torque output;

measuring the amplitude of the ripple signal;

comparing the ripple signal amplitude to the average peak torque amplitude to determine the amount of fusion in the torque record; and adjusting the stimulation frequency based on the determined amount of fusion until a selected amount of fusion is produced in the torque output record.

8. The method as claimed in claim 7, wherein the step of comparing the ripple signal amplitude to the torque amplitude comprises the steps of computing the ripple amplitude as a percentage of the total torque amplitude, and comparing the computed ripple percentage to a selected ripple percentage.

9. The method as claimed in claim 8, wherein the selected ripple percentage is in the range from 10% to 20%.

10. The method as claimed in claim 8, wherein the step of adjusting the stimulation frequency comprises decreasing the stimulation frequency by a selected increment if the computed ripple percentage is below the selected percentage, and increasing the stimulation frequency by the selected increment if the computed ripple percentage is above the selected percentage.

11. The method as claimed in claim 10, including the step of returning to the ripple percentage computing step after each adjustment of the stimulation frequency.

12. The method as claimed in claim 7, including the step of comparing the elapsed time to a selected treatment time when the selected amount of fusion is produced in the torque record, returning to the ripple amplitude measuring step if the elapsed time is less than said selected treatment time, and terminating application of the stimulation signal if the elapsed time is greater than the selected treatment time.

13. An apparatus for exercising skeletal muscles, comprising:

at least one stimulating electrode adapted to be electrically coupled to one or more muscles;

at least one stimulation means connected to said electrode for producing a selected electrical stimulation signal at said electrode for coupling into said muscles, the stimulation means comprising means for producing an output stimulation signal having a stimulation frequency and amplitude;

torque detection means for operatively coupling to said muscles for detecting torque output by said muscles during stimulation and producing a torque output signal having a superimposed ripple signal unless a fused contraction is induced in the muscles;

control means connected to said torque detection means for controlling said stimulation means to vary said stimulation frequency in response to said torque output signal, said control means having a stimulation frequency control output; and the control means including means for computing, from said torque output signal, an average peak torque amplitude and a ripple amplitude, means for computing a ripple percentage of said average peak amplitude, means for comparing the ripple percentage to a selected value, and means for adjusting said stimulation frequency control output to vary said stimulation frequency until said ripple percentage corresponds to said selected value.

14. The apparatus as claimed in claim 13, wherein said torque detection means comprises a wheatstone bridge strain gauge.

15. The apparatus as claimed in claim 13, wherein said selected value is in the range from 10% to 20%.

\* \* \* \* \*